US012669493B2

(12) United States Patent
Pechiney et al.

(10) Patent No.: US 12,669,493 B2
(45) Date of Patent: Jun. 30, 2026

(54) DIAGNOSTIC SYSTEM DIRECTLY CONNECTED TO A SUBTERRANEAN FORMATION FOR CARBON DIOIXDE MONITORING

(71) Applicant: Patina IP LLC, Richmond, TX (US)

(72) Inventors: John Jeffrey Pechiney, Houston, TX (US); Jason Michael Watford, Houston, TX (US)

(73) Assignee: Patina IP LLC, Houston, TX (US)

( * ) Notice: Subject to any disclaimer, the term of this patent is extended or adjusted under 35 U.S.C. 154(b) by 0 days.

(21) Appl. No.: 18/503,085

(22) Filed: Nov. 6, 2023

(65) Prior Publication Data

US 2024/0069003 A1     Feb. 29, 2024

Related U.S. Application Data

(63) Continuation-in-part of application No. 18/108,303, filed on Feb. 10, 2023.

(60) Provisional application No. 63/423,099, filed on Nov. 7, 2022, provisional application No. 63/358,541, filed on Jul. 6, 2022, provisional application No. 63/308,794, filed on Feb. 10, 2022.

(51) Int. Cl.
*G01N 33/28* (2006.01)
*E21B 41/00* (2006.01)
*E21B 49/08* (2006.01)

(52) U.S. Cl.
CPC ..... *G01N 33/2841* (2013.01); *E21B 41/0064* (2013.01); *E21B 49/086* (2013.01); *G01N 33/2823* (2013.01)

(58) Field of Classification Search
CPC .... E21B 49/086; E21B 41/0064; E21B 47/11; E21B 43/34; E21B 21/063; G01N 33/2823; G01N 33/2841; G01N 30/7026; G01N 21/64; G01N 1/14; G01N 33/2882; G01N 2021/6417; G01N 2030/025; G01N 2001/1025
See application file for complete search history.

(56) References Cited

U.S. PATENT DOCUMENTS

| | | | |
|---|---|---|---|
| 7,472,748 B2 | 1/2009 | Gdanski et al. | |
| 8,028,562 B2 | 10/2011 | Shah et al. | |

(Continued)

*Primary Examiner* — Yong-Suk (Philip) Ro
(74) *Attorney, Agent, or Firm* — Greene IP PLLC; Rachel E. Greene

(57) ABSTRACT

An apparatus and methods for characterizing and communicating carbon dioxide presence in a subterranean formation traversed by a wellbore including collecting fluid from the wellbore at a wellhead, analyzing the fluid for the presence, concentration, or both of the carbon dioxide using an instrument connected to a line collecting the fluid from the wellhead, and communicating the instrument analysis information within 24 hours of analyzing the fluid. Some embodiments may control the introduction of carbon dioxide into the formation. An apparatus and methods for monitoring the presence of carbon dioxide in a fluid produced from a wellbore including continuously collecting and conditioning a sample line from a wellbore, analyzing the sample line with an instrument at the wellsite, recording information from the analyzing continuously over time, and controlling the collecting, conditioning, analyzing, and recording with a process control device.

19 Claims, 9 Drawing Sheets

(56) References Cited

U.S. PATENT DOCUMENTS

| | | | |
|---|---|---|---|
| 8,332,194 B2 | 12/2012 | Morales et al. | |
| 8,636,524 B2 | 1/2014 | Montena et al. | |
| 11,327,197 B2 | 5/2022 | Jones et al. | |
| 2011/0320128 A1 | 12/2011 | Shook | |
| 2012/0103602 A1* | 5/2012 | Lackner ................ | B01F 25/316 |
| | | | 166/250.12 |
| 2013/0341012 A1* | 12/2013 | Belani ..................... | E21B 47/10 |
| | | | 166/250.12 |
| 2014/0124196 A1* | 5/2014 | Sunde ..................... | E21B 47/11 |
| | | | 166/250.12 |
| 2014/0260694 A1 | 9/2014 | Szlendak | |
| 2015/0130468 A1 | 5/2015 | Christian et al. | |
| 2017/0183955 A1* | 6/2017 | Peacock ................. | E21B 47/07 |
| 2017/0370210 A1 | 12/2017 | Nyhavn et al. | |
| 2018/0275114 A1 | 9/2018 | Kosynkin et al. | |
| 2020/0056471 A1 | 2/2020 | Ellis et al. | |
| 2022/0065101 A1 | 3/2022 | Poitzsch et al. | |

* cited by examiner

DIAGNOSTIC SYSTEM DIRECTLY CONNECTED TO A SUBTERRANEAN FORMATION FOR CARBON DIOIXDE MONITORING

PRIORITY CLAIM

This application claims priority to U.S. Provisional Patent Application Ser. No. 63/423,099, filed Nov. 7, 2022 entitled, "Diagnostic System Directly Connected to a Subterranean Formation for Carbon Dioxide Monitoring." This application also claims priority as a continuation in part application of U.S. patent application Ser. No. 18/108,303 filed Feb. 10, 2023, entitled, "Continuous Characterization and Communication of Chemical Tracer," which claims priority to U.S. Provisional Patent Application Ser. No. 63/308,794 filed Feb. 10, 2022, entitled Diagnostic System Directly Connected to a Subterranean Formation and U.S. Provisional Patent Application Ser. No. 63/358,541 filed Jul. 6, 2022, entitled Sample Conditioning for a Diagnostic System Directly Connected to a Subterranean Formation. All four applications are incorporated herein by reference in their entirety.

FIELD

Embodiments of the invention described herein relate to observing fluid to characterize physical properties of the fluid and formation using the presence and concentration of carbon dioxide.

BACKGROUND

There are many active carbon dioxide sequestration projects in the oil and gas industry. Carbon dioxide, a biproduct from a variety of economic activities, is transported from its source via pipeline or truck and injected into a disposal reservoir. The reservoir characteristics are such that it can hold significant amounts of carbon dioxide in its connected pore spaces and there is often a trap or seal to keep the carbon dioxide in the reservoir. Some disposal reservoirs are old and were depleted of their hydrocarbons in the early $20^{th}$ century and some are newly developed specifically for carbon dioxide sequestration.

To successfully dispose of any fluid in a subterranean formation several conditions must exist. The disposal reservoir must have sufficient pore space to contain the disposal fluid. Second, the pore spaces must have sufficient interconnectivity, i.e., permeability, so that the disposal fluid can flow into the far reaches of the reservoir from its injection point. Third, the reservoir must have a trap or seal so the disposal fluids are contained within the porous rocks and cannot leak out. FIG. 1 shows a diagram of a reservoir 1 that has these characteristics. The thickness of the porous and permeable reservoir rock 2 can in some cases be thousands of feet thick. Geographically these rocks can span hundreds to thousands of square miles and can hold significant amounts of fluids. FIG. 1 also shows injector wells 3 on the flanks of the reservoir 1 and monitoring wells 4 near the top or interior of the reservoir 1. The sectional view includes a seal of shale barrier 5, porous and permeable reservoir rock 2, and source rock that may also act as a shale barrier 6. FIGS. 2A and 2B illustrate rock grain structure to show the difference between porous and permeable rocks. FIG. 2A shows the disposal reservoir properties including flow pathways 7 and pore space 8 which are porous and permeable. FIG. 2B shows the seal reservoir properties, which are porous and impermeable because the seal contains pore space 9 but no flow pathways.

A bird's eye view of the injection operation is shown in FIG. 3. It is necessary to confirm that the carbon dioxide being injected into these reservoirs remains there and does not leak into adjacent formations or escape from the reservoir back onto the surface of the earth via a flow path. Monitoring wells 11 are typically drilled or already exist in the field and are useful for verifying that the injected carbon dioxide remains in the reservoir for the life of the injection and thereafter.

Each circle represents a well. The solid black circles with an arrow are the injector wells 10 where the $CO_2$ is injected into the disposal reservoir 1. Once the $CO_2$ exits its injection point via the injector well 10 and into the reservoir 1 it will flow via the path of least resistance through the permeable rock 2, as shown in FIG. 3. The white open circles are the monitoring wells 11 which are used to confirm the extent of the injection over time, the reservoir pressure, and to confirm the disposal fluids are sealed in the reservoir. As the disposal reservoir 1 is filled with the disposal fluid, $CO_2$, the void pore spaces of the rock 8 will fill and become pressurized. An adequate disposal operation will completely contain the $CO_2$ and none will be present in the monitoring wells 11. In the event the $CO_2$ is not properly sealed into the reservoir and escapes into a monitoring well 11, the injection must be halted and redesigned to avoid the leaking area. This can be done by sealing off the connection to the reservoir with a well intervention or by abandoning the leaking section and injecting into another part of the field.

SUMMARY

Embodiments of the invention described herein relate to an apparatus and methods for characterizing and communicating carbon dioxide presence in a subterranean formation traversed by a wellbore including collecting fluid from the wellbore at a wellhead, analyzing the fluid for the presence, concentration, or both of the carbon dioxide using an instrument connected to a line collecting the fluid from the wellhead, and communicating the instrument analysis information within 24 hours of analyzing the fluid. Some embodiments may control the introduction of carbon dioxide into the formation. In some embodiments, the collecting fluid and analyzing the fluid is continuous and may include conditioning a flow of fluid. Some embodiments may control the collecting, analyzing, and communicating using a controller. An autonomous system may be used to control the collecting, analyzing, and communicating. The system may include a multiplex valve that controls for multiple inputs. The multiple inputs may include time, wellhead identity, calibration, signals from the instrument or the controller, or a combination thereof. Some embodiments may further include analyzing for the presence or concentration or both of a hydrocarbon. In some embodiments, the instrument measures the fluid from the wellbore after a conditioning activity that may include fluid composition, fluid gas to liquid ratio, time between analyzing, phase separation, temperature control, pressure control, or a combination thereof. In some embodiments, the instrument has a line in direct communication with the wellbore. In some embodiments, the communicating comprises a transmitter to transmit a signal to a remote device.

An apparatus and methods for monitoring the presence of carbon dioxide in a fluid produced from a wellbore including continuously collecting and conditioning a sample line from a wellbore, analyzing the sample line with an instrument at the wellsite, recording information from the analyzing continuously over time, and controlling the collecting, conditioning, analyzing, and recording with a process control device. In some embodiments, the process control device is a microprocessor. The controlling may include communicating the information to a remote location. In some embodiments, the collecting, conditioning, analyzing, recording, and communicating occur within 10 minutes. In some embodiments, the collecting, conditioning, analyzing, recording, and communicating are repeated continuously over 24 hours. Some embodiments may adjust a heater or air conditioner.

DETAILED DESCRIPTION

Embodiments herein relate to collecting carbon dioxide concentration information at the wellsite that informs how to better manage a disposal reservoir. By directly connecting a diagnostic system to the reservoir wellbore, engineers have

Figure 4:
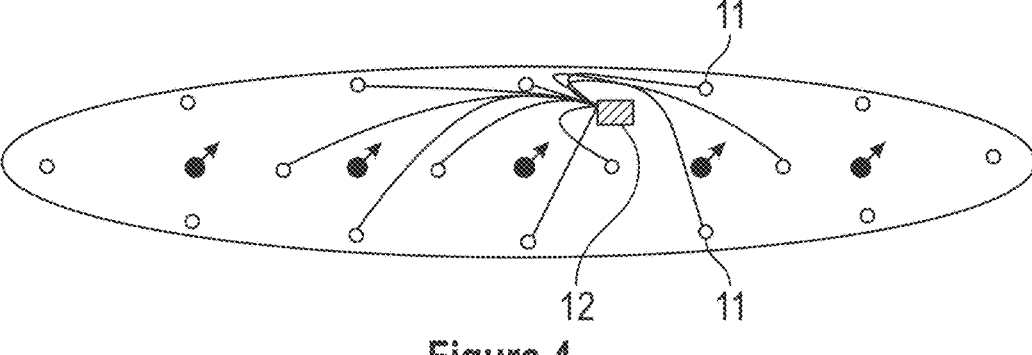
FIG. 4 is a schematic view of the surface of a disposal injection field with an enclosed trailer and instrument connected to several monitoring wells.

4 a faster system to optimize disposal operations and better understand well-to-well connections from a collection of wells.
In some embodiments an instrument is connected directly to the monitoring wellhead on the surface of the earth. In some embodiments, the instrument is the size of a carry-on suitcase with approximate dimensions of 22"×14"×9". Internal components include a gas-chromatograph, with a packed or capillary column, an oven, insulation, a detector, either electron-capture, flame-ionization, mass spectrometer, pulse discharge or ion-mobility spectrometer, a multiplexing valve, a computer, over-the-air communications electronics, and connection ports. All these components are assembled within the case. The instrument will also include carrier gas, either nitrogen or helium, calibration gases, and blank gases. In some embodiments, the gas-chromatograph is manufactured by and is commercially available from Agilent of Santa Clara, California, Thermo Fisher Scientific of Waltham, Massachusetts, G.A.S of Dortmund, Germany, or VICI of Houston Texas. The connection ports are manufactured by and are commercially available from Grainger of Lake Forest, Illinois.
In some embodiments the instrument and its accessories are housed in an enclosed trailer. In some embodiments the enclosed trailer is placed in the field so that it is central to the monitoring wells. From its central location several monitoring wells can be connected to the instrument and continuously sampled throughout the life of the disposal injection. FIG. 4 illustrates a trailer 12 placed in a central field location and connected to several monitoring wells 11.
In some embodiments, monitoring well gas will pass through a needle valve and through a line connected to the instrument. Monitoring well gas will flow into the gas chromatograph where the molecules will be separated then into the detector where the molecules will be quantified. After passing through the detector the gas will be collected via a vent line. If there is carbon dioxide in the sample the instrument will quantify the concentration, in parts per million (mg/l), parts per billion (ug/l) or parts per trillion (ng/l). In some embodiments the instrument can analyze for other components in the monitoring well gases: methane, oxygen, argon, nitrogen, carbon monoxide and heavier natural gas components such as ethane, pentane, or propane. In some embodiments the injection stream purity is useful to analyze. There will likely be other compounds in the stream of carbon dioxide, and it would be useful to know of the presence and their concentrations, i.e. sulfur dioxide, carbon monoxide, methane, etc.
In some embodiments it is useful to analyze for ratios of the components in the monitoring well gases. Methane is commonly referred to as C1, Ethane, C2, Propane C3, Butane C4, Pentane C5, and Hexane C6. Ratios such as C1/C5 are important markers in well gases. Other ratios can be considered such as Nitrogen/Argon or C4/C5.
The entire system is controlled by the computer. It executes three major processes: operation of the instrument, quantification of the monitoring well gas and transmission of the data. The computer decides when to activate the gas chromatograph, oven, and detector. It quantifies the raw data from the GC and detector into time, date, and concentration of the carbon dioxide and other gases in the sample. It then prepares the data to be sent over-the-air via the communications system. The communications systems take the data in packets, encrypts them, and transmits them via cell signal to a receiving computer or computer network.
Since the system is operating in real time and not delayed waiting for samples being taken manually in the field, then shipped and analyzed in a lab, several actions can be taken that were not possible before this technology. If the monitoring well is producing significant amounts of carbon dioxide that it wasn't before, the well or reservoir will be deemed leaking and injections can be halted. To remediate a leaking monitoring well or reservoir a suite of well logs can be taken to identify issues within the monitoring well or near-wellbore region. Carbon dioxide breakthrough would not have been discovered for several weeks to months using traditional manual sampling and lab analysis techniques. If a steady stream of carbon dioxide is found to be producing from the monitoring well injection operations can be halted and the reservoir and monitoring well evaluated. Several remedial options exist if consistent leaking of carbon dioxide is found: abandonment of the reservoir injection, plug and abandonment of the monitoring well, remediation of the monitoring well, remediation of the injection well.

Embodiments herein relate to collecting chemical composition and concentration information at the wellsite to inform and better manage a producing reservoir with more information and faster communication during well services. Some embodiments may have systems that help a user to characterize well-to-well connections from a collection of wells, identify and confirm the impact of introducing $CO_2$ into the earth, and more efficiently or effectively produce mature field hydrocarbons under secondary recovery. By directly connecting a diagnostic system to the reservoir wellbore, engineers have a faster system to optimize well performance, better understand well-to-well connections from a collection of wells, better understand the effectiveness and impact of $CO_2$ storage, and more efficiently produce mature fields under secondary recovery.

The process begins with the injection of $CO_2$. Once the well has been completed and prepared for startup, samples of the well fluids are collected and analyzed on a continuous basis. The data is delivered to the ultimate beneficiary within twenty-four hours after a quality control process.

Wellsite is a term used for the temporary or permanent intersection of the wellbore with the surface of the earth at a wellhead and its surrounding land surface. A wellhead may include a variety of valve configurations depending on the wellbore properties, the production of the wellbore, the equipment to be used to modify the wellbore or its surrounding formation, and how the collection of reservoir fluids is controlled. The wellsite, informally referred to as a pad, is configured for temporary or permanent surface equipment, parking, trailers for offices, operator rest, or lab huts, storage for totes, barrels, silos, or shipping containers, waste treatment and storage equipment, pump trucks, missiles, agitation tanks, cement mixers, or other equipment, storage, human workplace accommodations, etc. Wellsite locations typically measure 350 feet by 350 feet and can contain up to 20 wells. Sometimes those wells at the earth's surface are spaced 10 feet apart and their flowlines 10 feet apart or less.

Collecting fluid from the wellbore at a wellhead may include fluid in transit from the wellbore flowing directly though the wellhead and into a rigid stainless steel line, flexible tubing, stainless steel rigid tubing, or any other ongoing, continuous, enclosed flow of fluid. Connections, welding, flanges, separation tools, pressure regulators, valves or other devices may slow, but do not stop the flow of fluid for collecting. The fluid collection in most embodiments is not encumbered by human delay for physical sample collection, shut in for long term production delays, etc.

Figure 1:
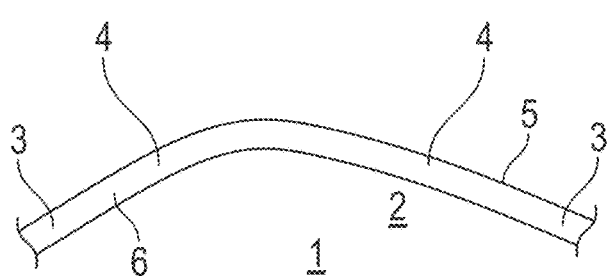
FIG. 1 is a sectional view of a formation traversed by monitoring wells and injection wells.
Figure 2A:
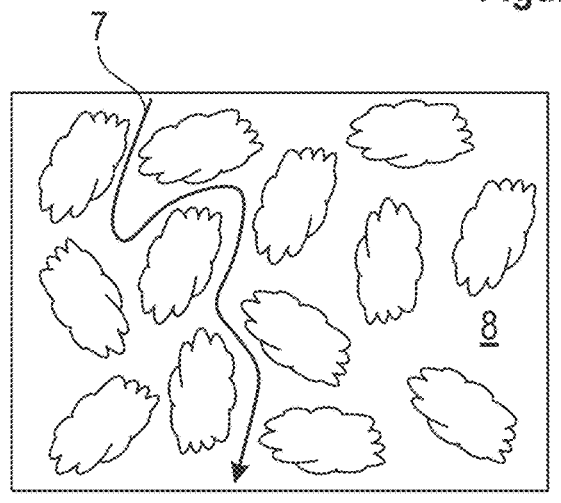
FIGS. 2A and 2B are schematic illustrations of subterranean rock grain structure for reservoir rock and seal rock.
Figure 2B:
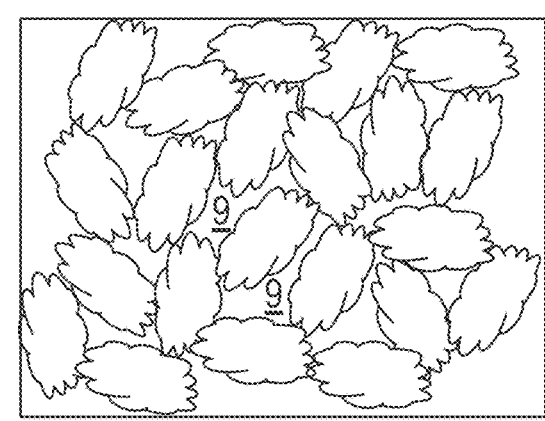
Figure 3:
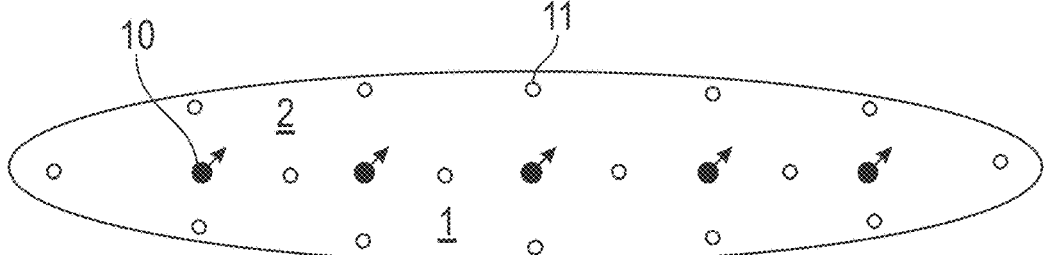
FIG. 3 is a schematic view of the surface of a disposal injection field.
Figure 5:
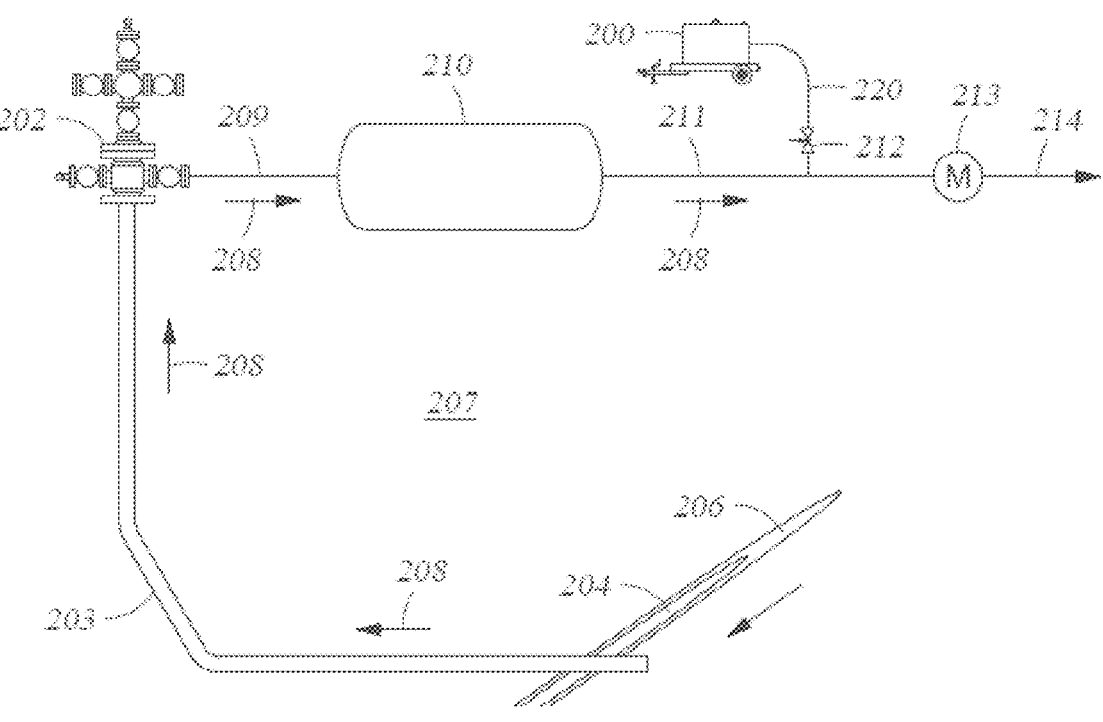
FIG. 5 is a schematic diagram of a flow path of reservoir fluids and tracers in a subterranean formation traversed by a wellbore at a wellsite with an embodiment of an instrument in communication with a needle valve.

FIG. 5 illustrates an embodiment with an instrument 200 in fluid communication with a needle valve 212. That is, FIG. 5 shows $CO_2$ 204 introduced into formation 207 traversed by a formation fracture 206 with a wellbore 203. Before the fluid from the reservoir 206 flows to the instrument 200 it travels through wellbore 203, a wellhead 202, a separator 210, and may continue through line meter 213. Flow lines 208 illustrate this flow. In some embodiments, the instrument 200 is the size of a carry-on suitcase with approximate dimensions of 22"×15"×10". Internal components include a gas-chromatograph, with a packed or capillary column; an oven; insulation; a detector; either flame-ionization, mass spectrometer, electron capture, or ion-mobility spectrometer, a multiplexing valve; a computer, over-the-air communications electronics; and connection ports. Some embodiments may include a pulse discharge helium ionization detector. All these components are assembled within the case. The instrument 200 will also include carrier gas, either nitrogen or helium, calibration gases, and blank gases. In some embodiments, the gas-chromatograph and its components are manufactured by and are commercially available from Agilent of Santa Clara, California, Thermo Fisher Scientific of Waltham, Massachusetts, G.A.S of Dortmund, Germany, VICI of Schenkon, Switzerland, or PID Analyzers of Sandwich, MA FIG. 2 shows the instrument 200 connected to the system via the needle valve 212 and tubing 220. Some embodiments may have slight variations in how the instrument 200 is engaged with the surface tubing and lines between the surface equipment shown with reference numerals 209, 211, and 214.

Figure 6:
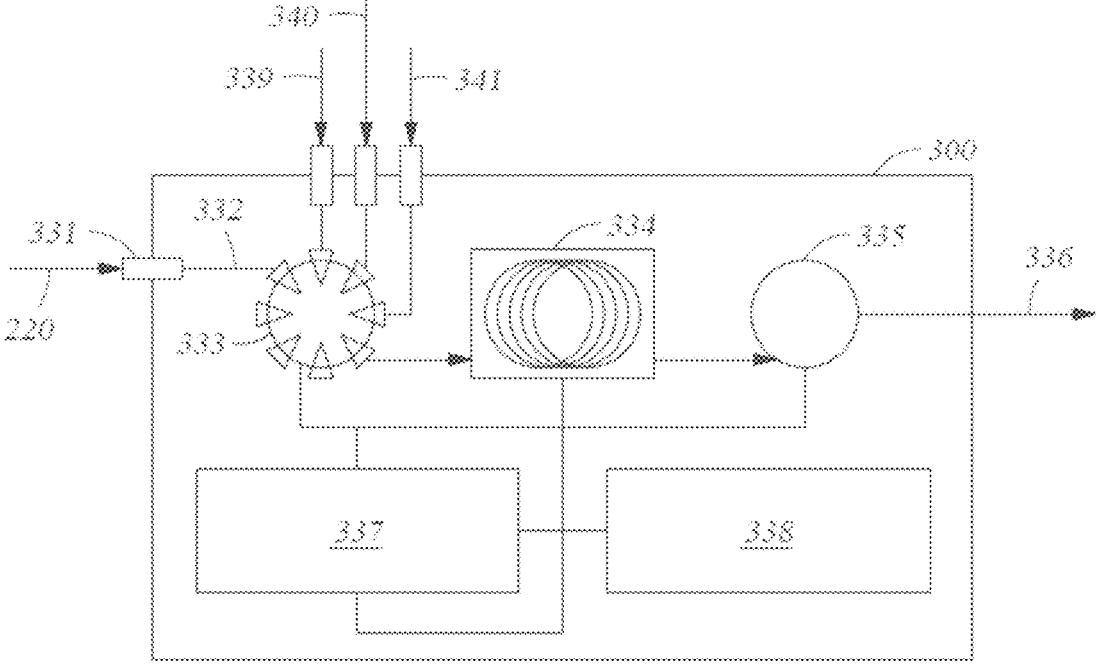
FIG. 6 is a schematic diagram of components within an embodiment of an instrument.

A case sectional view 300 is shown in FIG. 6. As the fluid containing $CO_2$ through the flowline 332 some fluid will pass through the line 220 from needle valve 212 and enter the instrument at connection 331. Calibration gas 339, blank gas 340, and carrier gas 341 will also enter the case. Fluid will pass through the multiplexing value 333, into the gas-chromatograph 334 where the gas molecules will be separated then into the detector 335 where the gas molecules will be quantified. After passing through the detector 335, the fluids will be collected via a vent line 336. The case 300 includes a computer or controller or process control device 337 and communications electronics 338.

Figure 7:
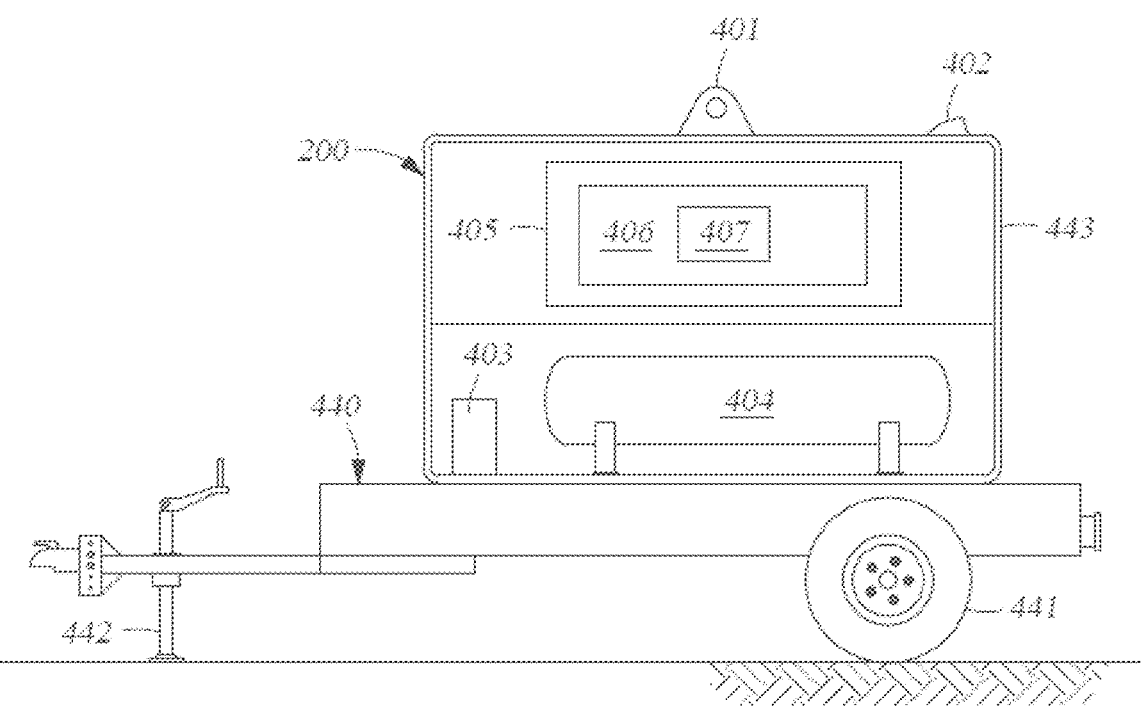
FIG. 7 is a schematic diagram of an embodiment of a utility trailer that includes an embodiment of an instrument with some components.
Figure 8:
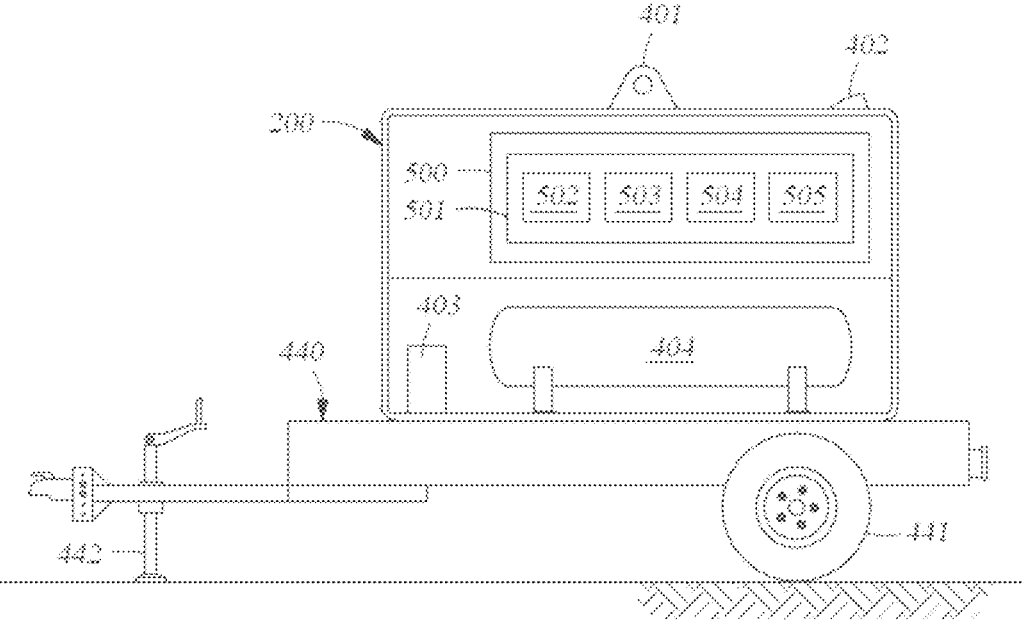
FIG. 8 is a schematic diagram of an embodiment of a utility trailer that includes an embodiment of an instrument with some components.

The physical system is illustrated in FIGS. 7 and 8 which show sectional views of an embodiment of a small trailer 440 that is configured for placement close to the production lines of the well, often directly in line with the wellhead 202. A mounting skid 443 houses the calibration gas 403 and carrier gas 404, and enclosure 405 protects the system from harsh weather. The enclosure 405 may enclose a heater or air conditioner (not shown). In some embodiments, the skid 443 and enclosure 405 house the electric equipment 406, maintain temperature control 407, and protects the electronics 406 from harsh weather. Also, the skid and enclosure 500 may include a computer (not shown in FIG. 7 or 8), gas chromatograph 501 with a detector, working gases 403, 404, gas purifiers (not shown in FIG. 7 or 8), a multi position valve (not shown in FIG. 7 or 8), a cellular antenna 402 and router 502, and an uninterrupted power supply 504, sample lines and sample inlet 505 to connect the production lines of a well to the gas chromatograph 503, and sample conditioning equipment (not shown in FIG. 7 or 8). A lifting hook 401, wheels 441, and jack 442 help with transport of the trailer 440.

The utility trailer 440 is about five feet wide by about ten feet long and weights about one thousand pounds. Sitting on top of the trailer 440 is the mounting skid 443, it is about five feet long, about three feet wide, and about four feet tall. It weighs about one thousand pounds. The mounting skid 443 is designed and manufactured to handle the harsh and rugged conditions of the field. Inside the bottom compartment of the mounting skid is a compressed cylinder of carrier gas 404 weighting about seventy five pounds and is about five feet long and about thirty inches in diameter. A small bottle of calibration gas 403 is about fifteen inches high, about four inches in diameter and weights about two pounds. On the top compartment of the mounting skid 443 sits the enclosure 405. The enclosure is about forty inches long, about thirty inches wide and about twenty inches tall and weighs about fifty pounds. The enclosure is ruggedized with high-strength powder-coated aluminum. It is designed to keep dust, wind, dirt, rain, ice and snow from contacting or affecting the electronics housed inside. Mounted to the side of the enclosure 405 is the temperature control unit 407 which is about fifteen inches high, about ten inches wide and about ten inches deep, the unit weighs about thirty pounds. The temperature control unit is designed to function in ambient temperatures of –40° C. to 40° C. and is designed to prevent dust, wind, dirt, rain, ice and snow from entering the enclosure while conditioning the air inside the enclosure to a set temperature. Sitting on top of the mounting skid 443 is a lifting eye 401, about four inches in diameter and a cellular antenna 402 which is about four inches in diameter and about three inches high and weights about two pounds. The cellular antenna is made of military grade rugged polymers and designed to function in harsh field conditions.

Inside the enclosure 405 is the gas chromatograph 503, about twenty four inches long, about nineteen inches wide and about eight inches high weighing about twenty pounds. The gas chromatograph is ruggedized with industrial grade electronics to withstand high temperatures and the stresses of field locations and movement from field location to field location. An uninterruptable power supply 504 has dimensions of about nineteen inches wide, about four inches high and about twelve inches long and weighs about twenty pounds. The uninterruptable power supply is constructed from industrial grade electronics and military grade materials. These units are designed to function in extremely harsh field locations such as war theaters. A cellular router 502 has dimensions of about four inches long, about three inches wide and about two inches tall weighing about one pound. The cellular router is also made of industrial grade and rugged materials and is designed to function in large changes in ambient temperatures in harsh field conditions. On the outside of the enclosure are the inlets 505 for the production lines to the wells, each inlet 505 is about one sixteenth of an inch in diameter.

Figure 9:
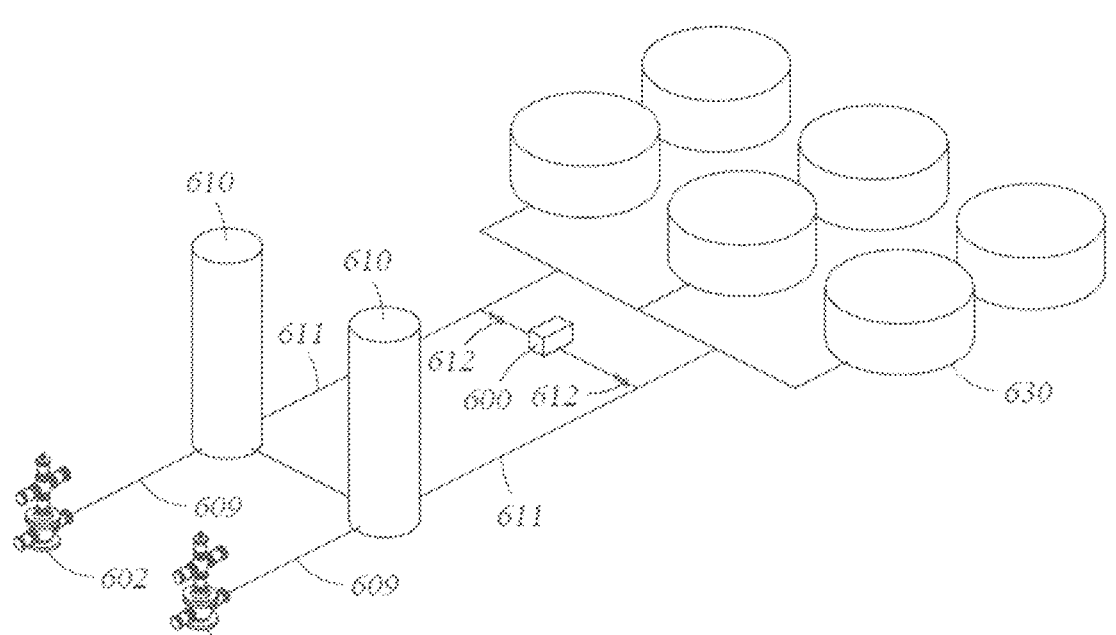
FIG. 9 is a dimensional view of a wellsite including embodiments of wellheads, separators, an instrument, and tank battery.

FIG. 9 is a three dimensional wellsite view that includes two wellheads 602, two separators 610, one instrument 600, and several tanks 630. The instrument 600 will be connected to the wellheads 602 where the tracers are expected to be produced via tubing 609. The instrument 600 will be placed downstream of the separator 610 near the metering equipment (not shown in FIG. 6), and next to the flow lines 611. FIG. 9 illustrates the relative size and location of the instrument 600 compared to the flow lines 609 and metering equipment 612.

Figure 10:
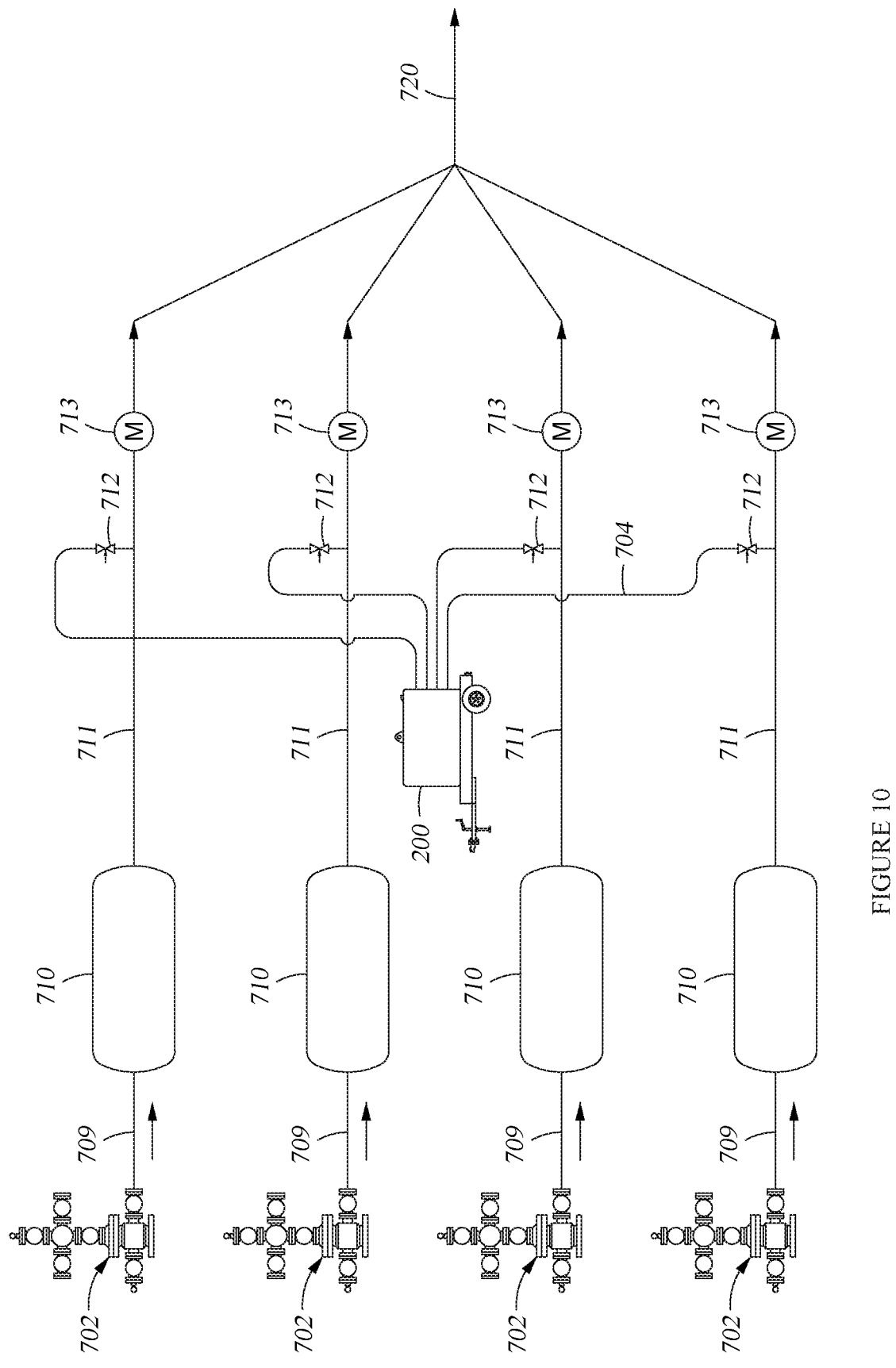
FIG. 10 is a schematic diagram of an embodiment of multiple wellheads, multiple separators, an instrument, and other components.

FIG. 10 illustrates the location of the instrument 200 at a wellsite with four wellheads 702. Each wellbore to be sampled is entered into a computer in instrument 200 or remotely in communication with instrument 200 by its name and position in the sequence. For example, well 1—sequence 1$^{st}$, well 2—sequence 2$^{nd}$, well 3—sequence 3$^{rd}$, well 4—sequence 4$^{th}$, calibration gas—sequence 5$^{th}$, blank gas—sequence 6$^{th}$. Once the sequence is entered a multi position valve housed in or nearby the instrument 200 is activated for each well. The flow rate from the wellhead 702 to the gas chromatograph in the instrument 200 is verified and set.

If a group of wells and wellheads 702 are positioned too far apart, typically greater than 100', a second instrument (not shown) similar to instrument 200 can be used. Each wellhead 702 will be connected to the instrument 200 with $\frac{1}{16}$ inch or $\frac{1}{4}$ inch stainless steel tubing 704 connected to the needle valve 712 on the flowline 711 from the separator 710. There may also be lines 709 to separators 710 before the fluid flows to the instrument 200. Some embodiments will bury the tubing 704 just below the ground or place a barrier over it to prevent tripping hazards. The tubing connections 704 connect into the multiplexing valve (not shown in FIG. 10) in the instrument 200. The calibration gases and blank gases will also connect into the multiplexing valve in or near the instrument 200. Power for the instrument will come from existing electricity sources at the field location, a battery pack, or a battery pack with solar charging capability. The power options will be determined by the field location and what is most accessible.

The multiplexing valve in instrument 200 allows for multiple inputs and one output. By closing off all the inputs but one then cycling to the next input, multiple flow streams can be sampled with one instrument. FIG. 10 also shows line meters 713, and line 720 to the main sales line or stock tank.

Figures 11A, 11B:
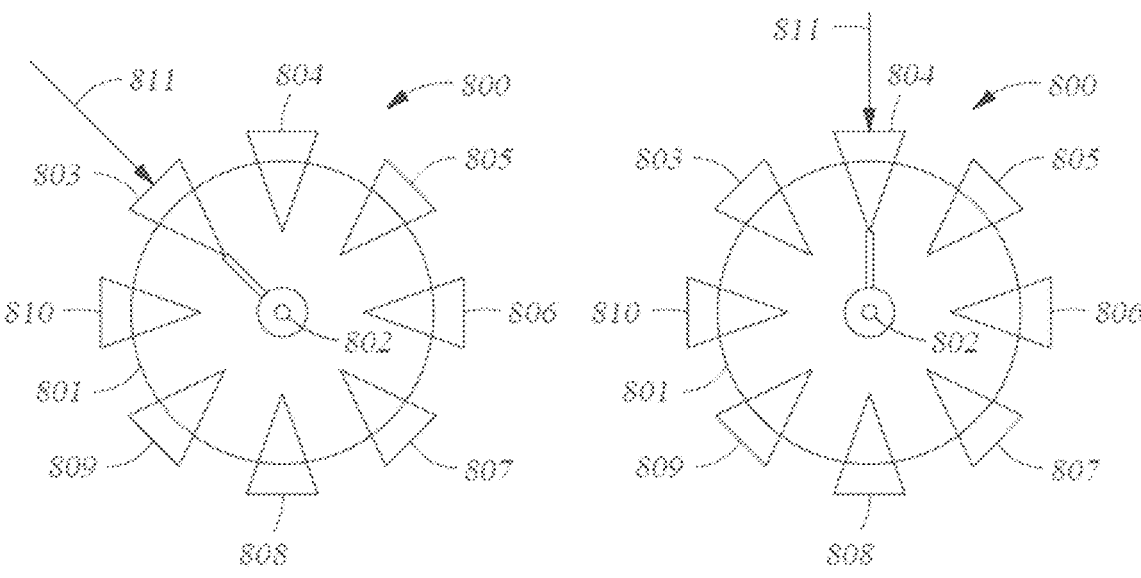
FIGS. 11A and 11B are schematic diagrams of embodiments of flow paths in an eight-input multiplexing valve.

FIGS. 11A and 11B show the flow paths of an eight-input multiplexing valve 801. FIG. 11A shows the inlet fluids 811 are coming into input 803 and exiting through the output 802 at the center of the valve. Inputs 804, 805, 806, 807, 808, 809, and 810 remain closed to flow. FIG. 11B shows the valve 801 has switched to connect inlet fluids 811 to input 804 while closing inputs 803, 805, 806, 807, 808, 809, and 810.

The operator will set the instrument to begin running on a schedule; this can be done by directly connecting to the instrument or remotely connecting to the instrument. The instrument and its communication electronics are accessed from anywhere in the world via cell or satellite signal. Once sampling is initiated the multiplexing valve will open and allow 1 microliter of fluid into the system. This will be joined by 10 microliters of carrier gas. The sample will then travel with the carrier gas into the gas chromatograph, then into the detector and finally deposited into a collection chamber or vented to the atmosphere. The system computer will record the data from the run and convert the raw data into time, date and concentrations present of each tracer, if there are tracers present in the sample. This sample analysis takes less than thirty minutes. In some embodiments, the duration of less than about 30 minutes is needed to analyze the fluid coming off the wellbore, i.e. natural gas coming into the instrument with $CO_2$ in it.

The data will then be encrypted and sent to the data collection platform via cell signal and the communication electronics. This means that tracers coming out of the reservoir minutes earlier are run through the instrument, analyzed, quantified, and delivered to the client in near real time. In addition, this can be done with multiple wells producing tracers by simply rotating the multiplexing valve. The multiplexing valve will rotate to allow fluids from the next well in the collection and the cycle will repeat. This is all done automatically according to a schedule set by the instrument operator and can be done from anywhere in the world. The instrument operator connects to the instrument like any networked computer, logs into operating system, opens the instrument control software and sets the run schedule. This consists of what positions the multiplexing valve will take and when, when a run will start and when the instrument is finished for the day. The system analyzes reservoir fluids in real time, essentially connected to the reservoir, and the schedule is modified by simply remote connecting into the instrument.

Further, in some embodiments, there are multiple fluids separated at a separator. For a gas well there may be water and gas, approximately, often 2 lines. For an oil well there may be water, oil, and gas, often 3 lines.

Next, we consider how the sample is conditioned. That is, embodiments herein relate to sample conditioning for collecting chemical composition and concentration information at the wellsite that informs how to manage a producing reservoir.

Practically speaking, water and oil expand when vaporized into gases in a gas chromatograph and can saturate the system causing it to malfunction. To separate the analytes of interest in a gas chromatograph they are heated to temperatures as high at 400° C. Even a tiny drop of liquid, such as 0.1 microliter, greatly expands as it evaporates into the gas phase in a gas chromatograph. Larger amounts of liquids expanding into the gas phase cause wear and tear on critical parts of the system. Some embodiments condition sample fluids before they enter the diagnostic system to ensure the accuracy and longevity of the equipment.

Figure 12:
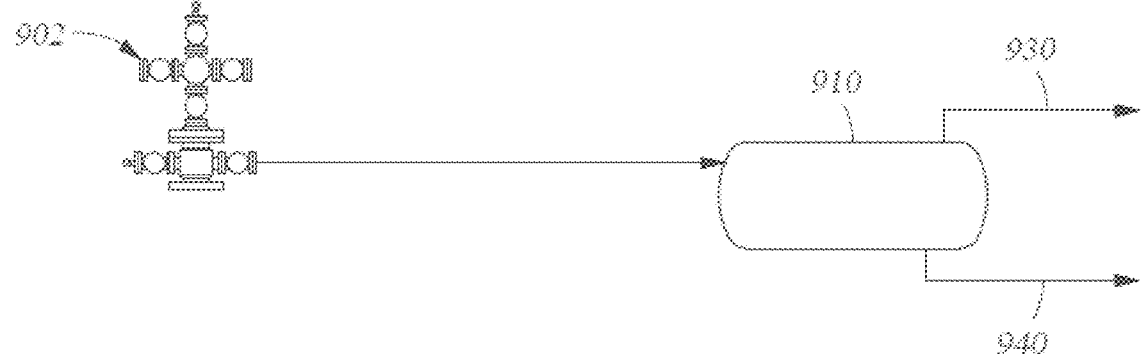
FIG. 12 is a schematic diagram of an embodiment of a separator in line with a wellhead and flow lines.
Figure 13:
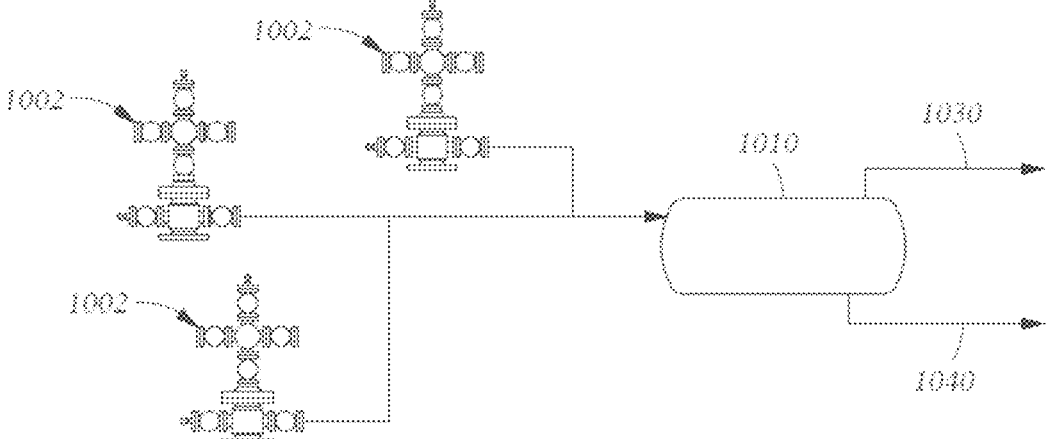
FIG. 13 is a schematic diagram of an embodiment of a separator in line with multiple wellheads and flow lines.

FIG. 12 illustrates an embodiment of an individual separation system and FIG. 13 illustrates an embodiment of a bulk separation. Production facilities of the embodiments described herein are designed in several configurations and may depend on the nature of the produced $CO_2$ and hydrocarbons, the rates at which the hydrocarbons are produced over time, and the operating philosophy of the well operator.

To accurately diagnose a well's performance and make changes to the well's operating conditions in real time, an individual sample of the oil or gas must be taken from each well. Comingled samples containing fluids from multiple wells do not provide sufficient information to optimize the reservoir flowing conditions. These individual samples will be before the bulk separation equipment and will need to be conditioned, i.e. the water or oil removed, before it is piped to the diagnostic system via 1/16" stainless steel lines.

The fluid properties of the hydrocarbons in the sales line or in the lines connected into the individual separator or bulk separator may also benefit from sample conditioning in some embodiments. Changing temperatures and pressures may cause components of natural gas to condense into liquids. Some embodiments benefit from conditioning these fluids to ensure the accuracy of the results and life of the diagnostic system. Since the system cannot handle liquid drops larger than 0.1 microliter, these natural gas liquids that may condense and degrade the system must be removed.

Sample conditioning equipment for some embodiments may be purchased from K2 Controls in Houston, Texas, Welker Inc. in Sugar Land, Texas or any other measurement and analysis company serving the pipeline, production, or distribution industries. In some embodiments, this equipment includes a 14"×6"×6" stainless-steel enclosure, 1/16" tubing, pressure ring, heater, 12" long probe, engineered membrane material, and/or 2'×2' water knockout. Some embodiments may include an air conditioner.

Some embodiments feature a direct connection to a diagnostic system that is sealed and tailored to include an appropriate pressure drop to ensure sample delivery to the diagnostic system. In a dry gas well where mainly methane is present the gas from the 4" line is piped through a 1/4" NPT, 4" long sample port through a pressure regulator then into 1/16" stainless steel tubing 5-30' to the diagnostic system.

The 4" sales line is typically elevated off the ground by 4' and has several 3/4" NPT sample ports, typically used for metering equipment. The diagnostic system requires low pressure sample gas and the pressure regulator drops the gas pressure from 150 psi to 15 psi.

Some embodiments feature a probe with an engineered membrane and a pressure regulator to ensure sample delivery to the diagnostic system. In a gas well where bulk separation is being used the engineered membrane will prevent water from entering the sample stream. The 12" long probe with a 2" engineered membrane tip is inserted in the fluid stream via a 3/4" NPT, 4" long sample port. A pressure regulator is attached to the top of the probe and then connected to 1/16" stainless steel tubing run 5'-30' to the diagnostic system. This configuration blocks any liquids in the flow stream and allows sample gas to flow to the diagnostic system.

Some embodiments feature a probe with an engineered membrane, a heated enclosure, and a pressure regulator to ensure sample delivery to the diagnostic system. In a gas well where bulk separation is being used the engineered membrane will prevent water from entering the sample stream. The heated enclosure with dimensions of 14"×6"×6" encases a 12" long probe with a 2" special membrane tip probe and a pressure regulator. The enclosure heats the gas to prevent heavier gas components from condensing in the sample stream. The heater temperature will be specific to the gas properties and chosen from the gas's phase diagram. The probe is inserted in the fluid stream via a 3/4" NPT, 4" long sample port. A pressure regulator is attached to the top of the probe and then connected to 1/16" stainless steel tubing run 5'-30' to the diagnostic system. This configuration blocks any liquids in the flow stream and allows gas to flow to the diagnostic system.

Some embodiments feature a water knockout system to ensure oil delivery to the diagnostic system. In oil wells where bulk separation is used a 2'×2' water knockout system is connected to the 4" flowline from the wellhead before the bulk separator. The water knockout acts as a mini separator allowing small volumes of oil to flow off the top. As the oil and water flow into the knockout the fluid slows down and allows the water to fall to the bottom of the water. The oil sitting on top of the water spills over the top and into 1/8" stainless-steel tubing that is connected to a 4" long, 3" in diameter stainless-steel vaporizing regulator that heats the oil and vaporizes the light components into a gas. The outlet of the regular is connected with 1/16" stainless-steel tubing and feeds the outlet vaporized gas into the diagnostic system.

Each of the hydrocarbon-based fluids can be described and characterized by their heat content measured in BTUs. Sampling conditioning will be determined by the fluid's heat content and dictate which conditioning system to use. Heat content depends on the carbon content present is the fluid. For example, low BTU gas or "dry" gas is comprised primarily of methane, C1. Mid to high BTU gas contains higher percentages of ethane, C2, and propane, C3, as well as iso-butane, n-butane and iso-pentane (iC4, nC4, iC5). Oil contains higher C content than C5, including hexanes (C6), heptanes (C7), octanes (C8), and all the way up to C30+.

Sample conditioning can be categorized into four categories when an individual separator is used:

Low btu gas on an individual separator

Mid to high btu gas on an individual separator

Low btu gas or oil on an individual separator

Mid to high btu gas or oil on an individual separator

Figure 14:
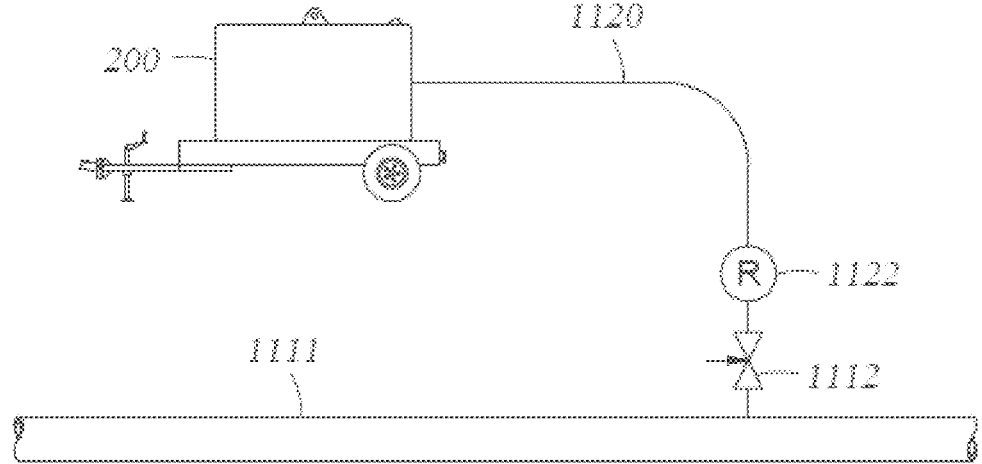
FIG. 14 is a schematic diagram of an embodiment of a gas flow line in communication with a diagnostic system.
Figure 15:
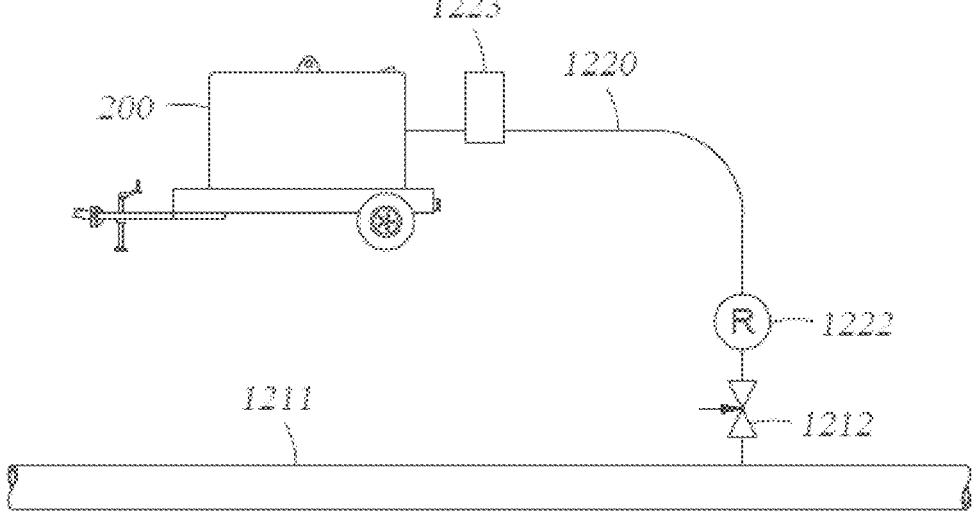
FIG. 15 is a schematic diagram of an embodiment of a gas flow line in communication with a diagnostic system.

Sample conditioning can be categorized into four categories when a bulk separator is used:

2-phase low btu gas and water on a bulk separator 2-phase mid to high btu gas and water on a bulk separator 3-phase low btu gas, water, and oil on a bulk separator 3-phase mid to high btu gas, water, and oil on a bulk separator A low btu gas on an individual separator case does not require conditioning since the gas is low btu and lacks components that condense during changes in pressure and temperature. The individual separator removes the water from the gas stream. The gas in this case is taken directly into the diagnostic system. A schematic for this embodiment is shown in FIG. 14, it is configured for a low btu gas and has no sample conditioning. FIG. 14 shows a gas flow line 1111, a valve 1112, a pressure regulator 1122, tubing 1120, and an instrument or diagnostic system 200. Mid to high btu gas flowing through an individual separator may require conditioning as the heavier components in the gas, such as propane, could condense when the pressure drops from the flow line to the diagnostic system. To maintain the gas phase a heated enclosure is needed as well as a membrane to ensure liquid droplets do not enter the diagnostic system. A schematic for this embodiment in shown in FIG. 15. FIG. 15 includes flowline 1211 with a pressure regulator 1222, a membrane and optional heater or heated enclosure 1223, stainless steel tubing 1220, and diagnostic system 200.

A low btu gas or oil on an individual separator system case does not require conditioning. If oil is the analysis fluid it can be connected directly to the vaporizing regulator then into the diagnostic system, if gas is the analysis fluid it is directly connected to the system as shown in FIG. 14.

A medium to high btu gas or oil on an individual separator system is like the other mid to high btu gas case, if the oil is the analysis fluid no conditioning is required. If gas is the analysis fluid a heated enclosure and membrane will be needed to maintain the gas phase, as illustrated in FIG. 15.

Figure 16:
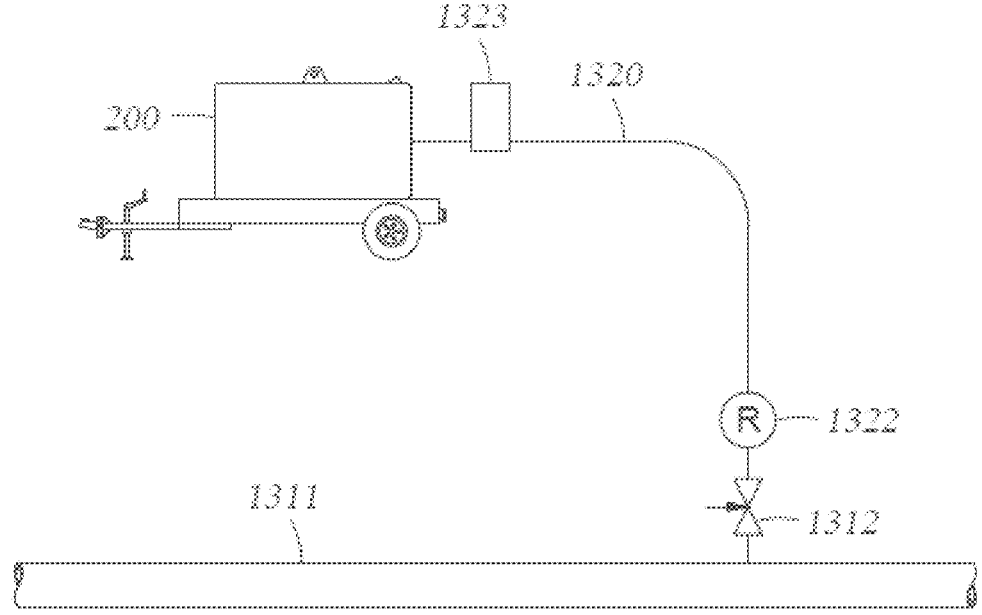
FIG. 16 is a schematic diagram of an embodiment of a gas flow line in communication with a diagnostic system.

A 2-phase low btu gas and water on a bulk separator system requires conditioning to separate the water and low btu gas upstream of the bulk separator. A probe is used to allow the gas to flow into the sample line while a membrane prevents any water from entering the diagnostic system. An embodiment of this is illustrated in FIG. 16. FIG. 16 shows a flowline 1311 with a pressure regulator 1322, probe and engineered membrane 1323, tubing 1320, and diagnostic system 200.

Figure 17:
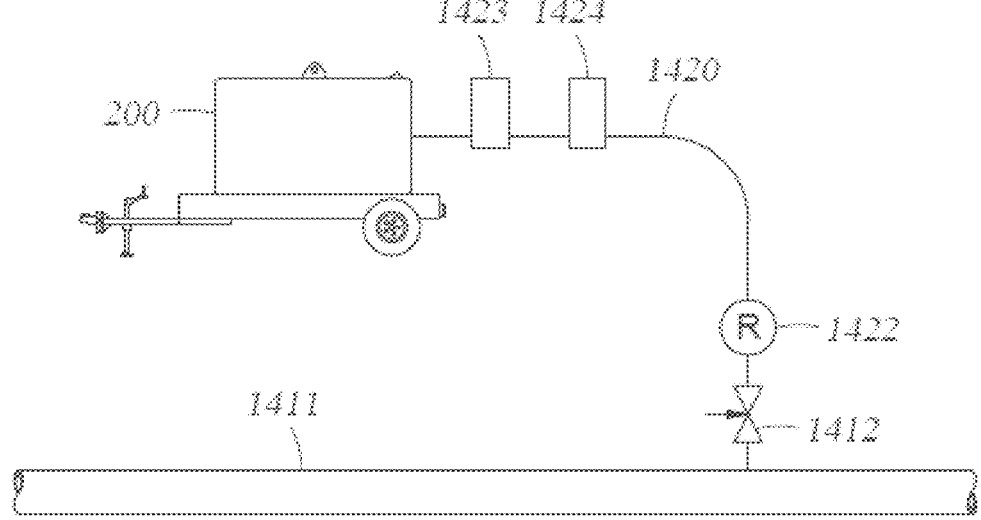
FIG. 17 is a schematic diagram of an embodiment of a gas flow line in communication with a diagnostic system.

A 2-phase mid to high btu gas and water on a bulk separator system may require a probe, heated enclosure, and membrane. That is, in addition to the probe and membrane needed to prevent water from entering the sample stream in the previous case, a heated enclosure is needed to maintain the gas phase preventing heavier gas components from becoming liquids. A sample probe, membrane, and heated enclosure setup is shown in FIG. 17. FIG. 17 includes flow line 1411 with a pressure regulator 1422, engineered membrane 1423, heated enclosure 1424 (these may be in the order shown in FIG. 17 or reversed in which one is in communication with the tubing 1420 first or housed in the instrument 200), tubing 1420, and diagnostic system 200.

Figure 18:
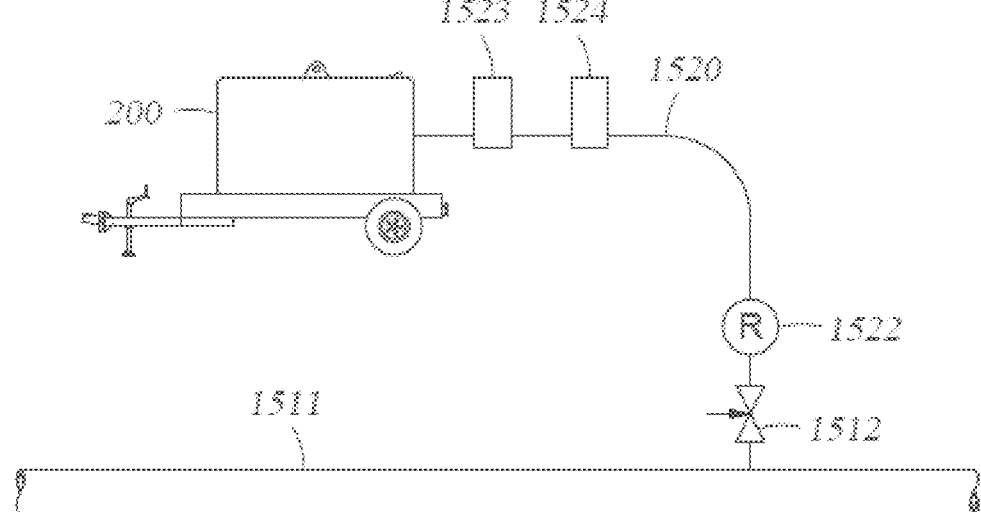
FIG. 18 is a schematic diagram of an embodiment of a gas flow line in communication with a diagnostic system.

A 3-phase low btu gas, water, and oil on a bulk separator system may include a hydrophobic probe and a membrane for oil. If gas is the analysis fluid, a sample probe with a membrane is needed to allow the gas to pass through and prevent the oil and water from entering the diagnostic system. This is illustrated in FIG. 16. If oil is the analysis fluid 2'×2' water knockout is needed to allow the oil the pass through but prevent the water and gas from entering the diagnostic system. This conditioning setup is shown in FIG. 18. FIG. 18 includes flow line 1511, sample probe 1502, water knockout 1524, vaporizing regulator 1523, tubing 1520, and diagnostic system 200. The water knockout 1524 and vaporizing regulator 1523 may be reversed in the order that they engage with tubing 1520 and may be enclosed in the instrument 200 in some embodiments.

Finally, a 3-phase mid to high btu gas, water, and oil on a bulk separator system may include the components as illustrated by FIG. 17 or 18. If gas is the analysis fluid a heated enclosure and membrane is needed to maintain the gas phase and prevent water and oil from entering the system as shown in FIG. 17. If oil is the analysis fluid a hydrophobic probe and membrane will be needed as shown in FIG. 18.

In some embodiments, the system is controlled by a controller or computer. It executes three major processes: operation of the instrument, quantification of the tracers and transmission of the data. The computer tells the multiplexing valve when to open and rotate, and when to activate the gas chromatograph, oven, and detector. It quantifies the raw data from the gas chromatograph and detector into time, date and concentration of the tracer. It then prepares the data to be sent over-the-air via the communications system. The communications systems takes the data in packets, encrypts them and transmits them via cell signal to a receiving computer or computer network.

The last part of the diagnostic system is the data delivery platform which consists of time, date, and concentration outputs of the CO2 from the instrument as well as well diagrams, field diagrams, formation diagrams, flowback schedules, production data, pressure data, and flowback data. The system together enables engineers to make decisions and changes to their operations in real time and validates whether their changes are effective.

Embodiments of the system have a methodical workflow with process steps that may be executed in the following order or with some variation. The system is mobilized to the wellsite and often placed as close as possible to the production lines as initial production begins. Samples lines are connected to each well and connected to the enclosure. Sample conditioning equipment is installed on the production lines. The system is plugged into a power source, either line power, a generator, or a bank of solar panels. The computer and gas chromatograph are turned on. The working gases, carrier, and calibration gas are set to their specified pressure and opened. The gas chromatograph is heated up to its specified temperature. The temperature control system is turned on. Communication to the system is tested with a cell phone or laptop connection.

Once the system has reached steady state, its temperature and working gases at their correct temperature, pressures and flow rates, a series of calibration runs are performed. Once the system is repeatability measuring its calibration gases, typically within 30 minutes of startup, it is time to program the system for sampling.

After the sequence is checked and flow rates are verified, it is time to begin sampling and analysis. The sequence is activated by flowing the production fluids into the gas chromatograph. The system will then activate the gas chromatograph sample loop and place the production fluid onto the column. As the sample flows through the column and into the detector the electronics and calibration stored in the computer will characterize the sample by chemical tracer and concentration. The multi position valve will then switch to the next well in the sequence and begin the process again. A sequence of four wells and one calibration gas will take about sixty minutes to complete. Once the sequence is complete the system will start a new sequence and remain sampling and analyzing for the duration of the project.

Once the system is sampling, a software application running on the computer will export the sample data into summary files describing the sample. Another software application will then look for these summary files on the system and transfer them to a cloud repository. This application continuously looks for newly exported files and when it finds them it initiates the transfer. The communications on the device function from a cellular router. Like the way a cell phone connects to the internet and transfers data to send emails, watch videos, or make phone calls, the cellular router acts as a wide area network and serves as the systems internet connection. Once the summary files are moved to the cloud another software application parses the summary files and transfers the data the proper tables in a relational database. By setting up a remote desktop application, such as Microsoft Remote Desktop or Logmein, the system can be connected to from an internet connection anywhere is the world. Once connected into the system via a remote desktop application a user can initiate a sample analysis sequence, check on the system's settings or even transfer data from the system to the user's computer.

After the data arrives in the cloud relational database it is output into a visualization containing the well, tracers, time and concentration. These data are quality checked, summarized, updated, and immediately released to the ultimate beneficiary via a web API or emailed file. At this point the beneficiary has received a significant number of samples in significantly faster timeframe and can act to manage the reservoir.

The control system for the device works on a series of events preprogrammed into the gas chromatograph commonly referred to as a method. Human machine interface software, such as Agilent's ChemStation, allows the user to program the events of the method. When a sample sequence is started a sample is run according to the method setup for a given length of time. Once that time is up the system will switch to next sample line and repeat the process.

The chemical identity and concentration test results are typically organized and help inform models of the reservoir into two major categories: Flow profiles and interwell communication.

Interwell communication describes how the reservoir fluids flow in relation to wells over time. Tracers pumped in one well and recovered in another implies fluid communication through the reservoir. In secondary recovery operations, long-term well communication is preferred so that the injected fluids sweep more hydrocarbons. In hydraulically fractured wells, interwell communication can describe how the fracture system is propagating through the reservoir and traveling to another well, how natural fracture swarms or faults may magnify communication from one well to another, and how depleted reservoir rock affects fluid travel.

We claim:

1. A method for characterizing and communicating carbon dioxide presence in a subterranean formation traversed by a wellbore, comprising:
   collecting fluid from the wellbore at a wellhead;
   analyzing the fluid for the presence, concentration, or both of the carbon dioxide using an instrument connected to a line collecting the fluid from the wellhead; and
   wherein the collecting fluid and analyzing the fluid is continuous; and
   communicating the instrument analysis information within 24 hours of analyzing the fluid.

2. The method of claim 1, further comprising controlling the introduction of carbon dioxide into the formation.

3. The method of claim 1, wherein the instrument is a gas chromatograph.

4. The method of claim 1, wherein the collecting fluid comprises conditioning a flow of fluid.

5. The method of claim 1, further comprising controlling the collecting, analyzing, and communicating using a controller.

6. The method of claim 5, wherein the collecting fluid comprises an autonomous system.

7. The method of claim 6, wherein the autonomous system comprises a multiplex valve that controls for multiple inputs.

8. The method of claim 7, wherein the multiple inputs comprise time, wellhead identity, calibration, signals from the instrument or the controller, or a combination thereof.

9. The method of claim 1, wherein the analyzing further comprises analyzing for the presence or concentration or both of a hydrocarbon.

10. The method of claim 1, wherein the instrument measures the fluid from the wellbore after a conditioning activity.

11. The method of claim 10, wherein the conditioning activity comprises fluid composition, fluid gas to liquid ratio, time between analyzing, phase separation, temperature control, pressure control, or a combination thereof.

12. The method of claim 1, wherein the instrument has a line in direct communication with the wellbore.

13. The method of claim 1, wherein the communicating comprises a transmitter to transmit a signal to a remote device.

14. A method for monitoring the presence of carbon dioxide in a fluid produced from a wellbore, comprising;
   continuously collecting and conditioning a sample line from a wellbore;
   analyzing the sample line with an instrument at a wellsite;
   collecting the fluid and analyzing the fluid is continuous;
   recording information from the analyzing continuously over time; and
   controlling the collecting, conditioning, analyzing, and recording with a process control device.

15. The method of claim 14, wherein the process control device is a microprocessor.

16. The method of claim 14, wherein the controlling further comprises communicating the information to a remote location.

17. The method of claim 16, wherein the collecting, conditioning, analyzing, recording, and communicating occur within 10 minutes.

18. The method of claim 17, wherein the collecting, conditioning, analyzing, recording, and communicating are repeated continuously over 24 hours.

19. The method of claim 14, wherein the controlling further comprises adjusting a heater or air conditioner.

* * * * *